United States Patent [19]

Lukacs et al.

[11] Patent Number: 4,918,058
[45] Date of Patent: Apr. 17, 1990

[54] MACROLIDE COMPOUNDS

[75] Inventors: Gabor Lukacs; Catherine Duchatelle-Ruggeri, both of Paris, France

[73] Assignee: Adir Et Cie, Neuilly-sur-Seine, France

[21] Appl. No.: 191,270

[22] Filed: May 6, 1988

[30] Foreign Application Priority Data

May 6, 1987 [FR] France ............................. 87 06361
Jan. 7, 1988 [FR] France ............................. 88 00078
Jan. 29, 1988 [FR] France ............................. 88 01031

[51] Int. Cl.$^4$ ........................ A61K 31/70; C07H 17/08
[52] U.S. Cl. ......................................... 514/30; 536/7.1
[58] Field of Search ........................... 536/7.1; 514/30

[56] References Cited

U.S. PATENT DOCUMENTS 4,452,784  6/1984  Kirst et al. ............................. 536/7.1
4,668,776  5/1987  Yamada et al. ......................... 536/7.4

Primary Examiner—Johnnie R. Brown
Assistant Examiner—Elli Peselev
Attorney, Agent, or Firm—Gordon W. Hueschen

[57] ABSTRACT

Compounds of general formula:

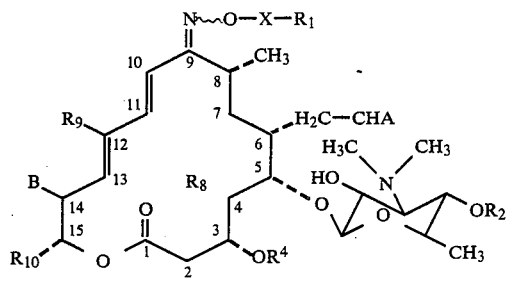

in which:

A denotes either an oxygen atom, or a group of the formula $N\sim O-Y-R_5$, $\sim$; B, X, Y, $R_1$, $R_2$, $R_3$, $R_4$, $R_5$, $R_8$, $R_9$ and $R_{10}$ being defined in the description.

Medicinal products containing the same, and their use in broad-spectrum antibiotic therapy for the treatment of infections.

30 Claims, No Drawings

MACROLIDE COMPOUNDS

The present invention relates to new antibiotics of the macrolide family, a process for the preparation thereof and pharmaceutical compositions containing them.

The needs of therapy demand the constant development of new antibiotics, both as a result of the possibility of appearance of new resistant strains, and also with the object of creating new molecules possessing improved activity in respect of both their threshold of efficacy and the breadth of their spectrum of action.

Many modifications of the macrolide ring-system have already been carried out in order to produce advantageous new antibiotics. Among the most recent, U.S. Pat. Nos. 4,528,369, 4,581,346 and 4,629,786 and European patent applications No. 0,103,465, 0,104,028, 0,154,495 and 0,203,621 may be mentioned.

More especially, the subject of the present invention is the macrolide compounds of general formula: (I)

[Structural formula of macrolide compound with positions 1–15 labeled, showing N∼O—X—R$_1$, CH$_3$, H$_2$C—CHA, H$_3$C, CH$_3$, HO, OR$_2$, OR$_4$, R$_8$, R$_9$, R$_{10}$, B substituents]

in which:

A denotes:
either an oxygen atom,
or a group of formula N∼O-Y-R$_5$,
the sign ∼ present in the substituent on carbon as well as in the definition of A meaning that one or other, independently, of the oxime or oxime ether groups can each be in the syn or anti form or in the form of a syn and anti mixture, X and Y, which may be identical or different, denote either a linear or branched alkyl radical containing at most ten carbon atoms, or a linear or branched alkenyl radical containing at most ten carbon atoms, or a linear or branched alkynyl radical containing at most ten carbon atoms, it being possible for each of the alkyl, alkenyl, or alkynyl substituents to be optionally substituted with one or more groups chosen from hydroxy, linear or branched lower alkyl, linear or branched lower alkenyl, linear or branched lower alkynyl, linear or branched lower alkenyloxy, linear or branched lower alkenylthio, linear or branched lower alkynyloxy, linear or branched lower alkynylthio, fluoro, chloro, bromo, iodo, amino or lower dialkylamino, R$_1$ and R$_5$, which may be identical or different, denote:
either a hydrogen atom, or a linear or branched alkyloxy radical containing at most ten carbon atoms, a linear or branched alkylthio radical containing at most ten carbon atoms, a linear or branched alkenyloxy radical containing at most ten carbon atoms, a linear or branched alkenylthio radical containing at most ten carbon atoms, a linear or branched alkynyloxy radical containing at most ten carbon atoms, a linear or branched alkynylthio radical containing at most ten carbon atoms, an aryl radical (by way of example, phenyl, pyridyl, thienyl, furyl, benzothienyl, benzofuryl, indolyl, thiazolyl, oxazolyl, pyrrolyl, imidazolyl, pyrazolyl, isothiazolyl, isoxazolyl, benzimidazolyl may be mentioned), an aryloxy, arylthio, aralkyloxy or aralkylthio radical, it being possible for each of the alkyloxy, alkylthio, alkenyloxy, alkenylthio, alkynyloxy, alkynylthio, aryl, aryloxy, arylthio, aralkyloxy or aralkyltho radicals to be optionally substituted with one or more radicals chosen from hydroxy, lower alkyl, lower alkenyl, lower alkynyl, lower alkyloxy, lower alkenyloxy, lower alkynyloxy, lower alkylthio, lower alkenylthio, lower alkynylthio, fluoro, chloro, bromo, iodo, nitro, amino or lower dialkylamino, or a radical N R$_6$ R$_7$ defined below,
or a radical $$-N\begin{matrix}R_6\\R_7\end{matrix}$$

in which R$_6$ and R$_7$, which may be identical or different, denote a hydrogen atom or a lower alkyl, lower alkenyl or lower alkynyl radical, or form, with the nitrogen, a saturated or unsaturated heterocyclic system optionally containing another hetero atom and optionally substituted with a halogen atom or a lower alkyl radical,
a chlorine, bromine, iodine or fluorine atom,
a carboxyl group, free or salified with an inorganic base (KOH, NaOH, Ca(OH)$_2$) or organic base (triethylamine, diethylamine, etc.) or esterified with an aliphatic alcohol of formula R$_8$OH where R$_8$ is a lower alkyl group,
or X—R$_1$ and Y—R$_5$, independently of one another, each denote a hydrogen atom, R$_2$ denotes
either a hydrogen atom,
or a radical of formula:

[Structural formula showing OH, CH$_3$, O, CH$_3$, OR'$_2$ substituents]

in which R'$_2$ denotes a hydrogen atom, a linear or branched lower alkyl radical or a linear or branched lower acyl radical, B denotes
either a hydrogen atom,
or a radical of formula:
—CH$_2$—O—B', where B' denotes:
either a hydrogen atom,
or a radical of formula:

[Structural formula showing R$_3$O, CH$_3$, O, OCH$_3$, OCH$_3$ substituents]

in which R$_3$ denotes a hydrogen atom or a linear or branched lower alkyl radical, R$_4$ denotes either a hydrogen atom,
or a linear or branched lower alkyl radical,
or a linear or branched lower acyl radical, $R_8$ denotes either a lower alkyloxy radical and preferably methoxy when B denotes a hydrogen atom, or a lower alkyl radical and preferably methyl when B denotes a group $-CH_2-O-B'$, $R_9$ denotes either a hydrogen atom when B denotes a hydrogen atom, or a lower alkyl radical and preferably methyl when B denotes a radical $-CH_2-O-B'$, $R_{10}$ denotes a lower alkyl radical, lower alkyl, lower alkyloxy, lower alkylthio, lower alkenyl, lower alkenyloxy, lower alkenylthio, lower alkynyl, lower acyl, lower alkynyloxy and lower alkynylthio radicals being understood to mean groups containing between 1 and 6 atoms.

The invention also encompasses the salts of the compounds of formula (I). Among acids which may be added to the compounds of formula (I) to form an addition salt, hydrochloric, hydrobromic, hydriodic, sulfuric, acetic, propionic, trifluoroacetic, maleic, malic, tartaric, methanesulfonic, ethanesulfonic, benzenesulfonic, ptoluenesulfonic, phosphoric, fumaric, citric and camphoric acids, etc., may be mentioned by way of example.

More especially, the present invention relates to the compounds in which:

1/ A is an oxygen atom,
X is a linear or branched lower alkyl radical,
$R_1$ is
a hydrogen atom,
an alkyl radical,
an aryl radical optionally substituted with a nitro group,
an alkenyloxy radical,
an alkyloxy radical optionally substituted with a lower alkyloxy radical,
a dialkylamino radical,
a nitrogen-containing heterocycle optionally containing another heteroatom,
an aryloxy or aralkyl radical, or $X-R_1$ denotes a hydrogen atom,
B, $R_2$, $R_4$, $R_8$, $R_9$ and $R_{10}$ have the same meanings as those stated above;

2/ A is a radical of formula N   $-O-Y-R_5$ in which the sign   has the same meaning as that stated above, and B, $R_1$, $R_2$, $R_3$, $R_4$, $R_8$, $R_9$, $R_{10}$ and X have the meanings stated in 1/,
Y is a linear of branched lower alkyl radical, and
$R_5$ is
a hydrogen atom,
an alkyl radical,
an alkyloxy radical optionally substituted with a lower alkyloxy radical,
or $Y-R_5$ denotes a hydrogen atom,
or $X-R_1$ and $Y-R_5$ each simultaneously denote a hydrogen atom.

Especially advantageous compounds of the present invention are those for which A, X, Y, $R_1$ and $R_5$ have the meaning stated in 1/ and 2/, and for which, on the one hand, B denotes a hydrogen atom while $R_8$ denotes a methoxy group, $R_9$ a hydrogen atom and $R_{10}$ a methyl group, or on the other hand, B denotes a group:

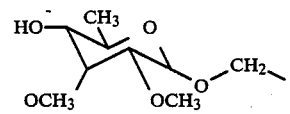

while $R_8$ and $R_9$ simultaneously denote a methyl group and $R_{10}$ an ethyl group.

The present invention also emcompasses a process for the preparation of the compounds of formula (I), which process employs as starting material, either, when B denotes a hydrogen atom, a compound of formula (II/1):

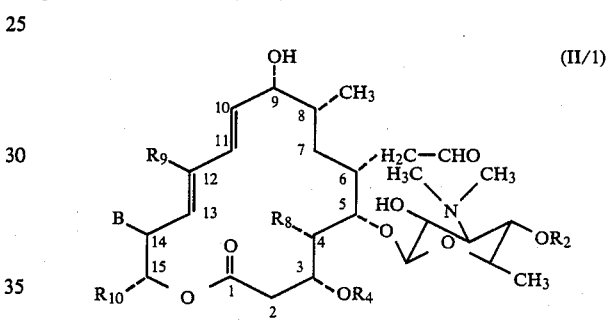

(II/1)

in which $R_2$, $R_4$, $R_8$ and $R_{10}$ have the same definition as in formula (I), B and $R_9$ each simultaneously denoting a hydrogen atom, which is subjected to an oxidizing agent such as, for example, the sulfur trioxide/pyridine complex in the presence of a basic agent such as an organic amine, in an organic medium preferably chosen from dimethyl sulfoxide, dimethylformamide and pyridine, to obtain a compound of formula (II/1a):

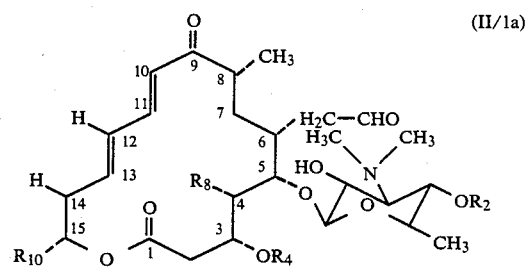

(II/1a)

in which $R_2$, $R_4$, $R_8$ and $R_{10}$ have the same meaning as in the formula (I), or, when, in the compound of formula (I), which it is desired to obtain, B and $R_9$ do not both simultaneously denote a hydrogen atom, a compound of formula (II/2):

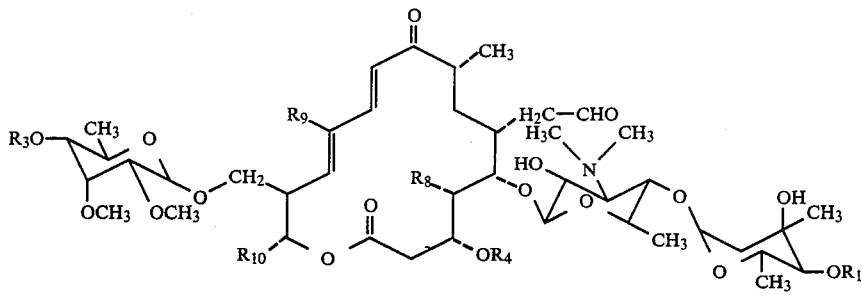

(II/2)

in which R'$_2$, R$_3$, R$_4$ and R$_{10}$ have the same definition as in the formula (I), and R$_8$ and R$_9$ denote a lower alkyl radical, preferably methyl, which, when, in the compound of formula (I) which it is desired to obtain, B' and R$_2$ simultaneously denotes a hydrogen atom, is in the first place subjected to the action of dilute hydrochloric acid of normality between 0.05 and 0.4, preferably between 0.1 and 0.30 and preferably between 0.15 and 0.25, at room temperature to lead, after washing with a suitable organic solvent, alkalinization and extraction with a suitable organic solvent, to a derivative of formula (II/2a):

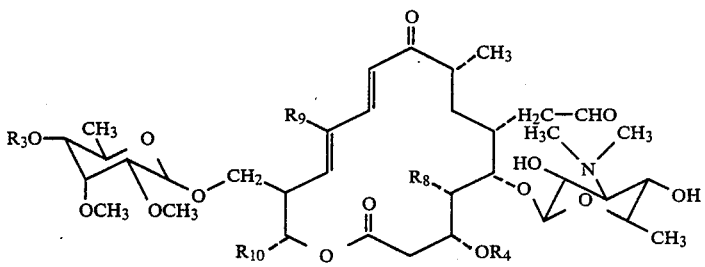

(II/2a)

in which R$_3$, R$_4$ and R$_{10}$ have the same meaning as in the formula (I), and R$_8$ and R$_9$ have the same meaning as in the formula (II/2), which is reacted with dilute hydrochloric acid of normality between 0.25 and 0.75, preferably between 0.3 and 0.7, and preferably between 0.4 and 0.6, at a temperature preferably between 30° and 100° C., preferably between 50° and 90° C., and preferably between 70° and 80° C., to lead, after washing with a suitable organic solvent, alkalinization and extraction with a suitable organic solvent, to a compound of formula (II/2b):

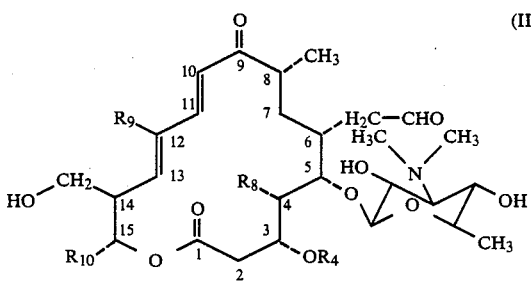

(II/2b)

in which R$_4$ and R$_{10}$ have the same meaning as in the formula (I), and R$_8$ and R$_9$ have the same meaning as in the formula (II/2), which is optionally purified by chromatography on a silica column, the compound thus chosen, of general formula (II/1a) or (II/2) or (II/2b) depending on the compound of formula (I) which it is desired to obtain, then being condensed with an alcohol of formula Z—OH, in which Z denotes a lower alkyl group, in the presence of an acid catalytic agent such as para-toluenesulfonic acid, or preferably difluoroacetic acid when the compound of formula (I) which it is desired to obtain has a radical R$_2$ other than H, the reaction medium then being subjected to the action of a basic agent, especially an amine such as triethylamine, to obtain, after extraction with an organic solvent preferably chosen from diethyl ether, chloroform and methylene chloride, and purification by chromatography on a silica column, a compound of formula (III):

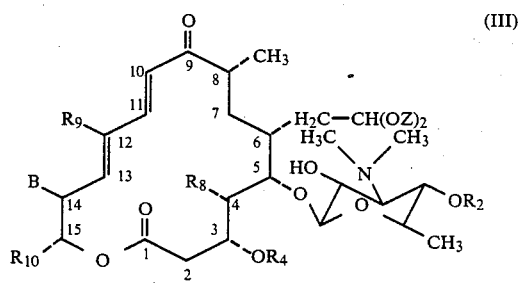

(III)

in which B, R$_2$, R$_4$, R$_8$, R$_9$ and R$_{10}$ have the same meaning as in the formula of the chosen derivative (II/1a), (II/2) or (II/2b) and Z has the same definition as above, which is condensed in the presence of a base such as, for example, pyridine, triethylamine or an alkali metal salt such as sodium acetate or sodium hydrogen carbonate or potassium hydrogen carbonate or sodium carbonate or potassium carbonate or calcium carbonate, either with a compound of formula (IV):

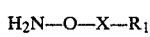

H$_2$N—O—X—R$_1$      (IV)

in which X and R$_1$ have the same meaning as in the formula (I) with the exception of the case in which X—R$_1$ denotes a hydrogen atom, or preferably with a strong acid salt (hydrochloride, hydrobromide, etc.) of such a product to obtain, after optional purification by chromatography on a silica column, a compound of formula (V):

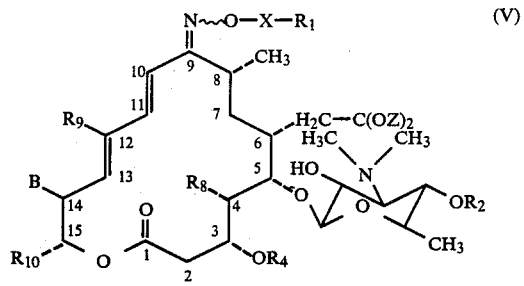

in which the sign ∼∼, X, R$_1$, R$_2$, R$_4$, R$_8$, R$_9$, R$_{10}$ and B have the same meaning as in the formula (III) and Z the same definition as above, or with a strong acid salt of hydroxylamine to obtain a compound of formula (V/a):

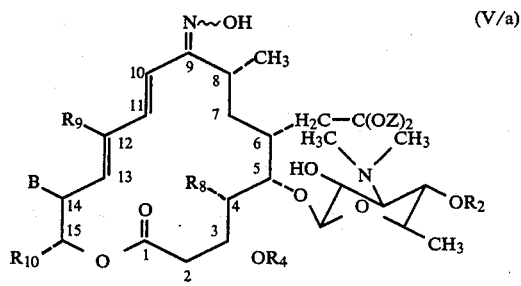

which is a special case of compounds of formula (V) in which the sign ∼∼, B, R$_2$, R$_4$, R$_8$, R$_9$, R$_{10}$ and Z have the same meaning as in the formula (V), X—R$_1$ in this case denoting a hydrogen atom, which is treated, where appropriate, in the presence of a base such as, for example, triethylamine or pyridine, or an alkali metal salt such as sodium carbonate or potassium carbonate or calcium carbonate or sodium hydrogen carbonate or potassium hydrogen carbonate, or an alkali metal hydride such as sodium hydride, in a solvent preferably chosen from pyridine, acetone, dimethylformamide, dioxane, acetonitrile, tetrahydrofuran and diethyl or diisopropyl ether, with a compound of formula (VI):

$$R_1—X—T \quad (VI)$$

in which T denotes a halogen atom and R$_1$ and X have the same meaning as in the formula (I), with the exception of the case in which R$_1$ and X together form a hydrogen atom, to obtain, after optional purification by chromatography on a silica column, a product of formula (V) in which the sign ∼∼, X, R$_1$, R$_2$, R$_4$, R$_8$, R$_9$, R$_{10}$ and B have the same meaning as in the formula (I) and Z the same meaning as in the formula (III), which, irrespective of the process according to which it has been obtained, in subjected to a customary process for deprotection of the aldehyde group carried by the carbon outside the ring at the β-position with respect to carbon$^6$, such as, for example, the action of an aqueous solution of hydrochloric acid of normality between 0.1N and 0.5N, preferably between 0.02N and 0.2N, preferably between 0.05N and 0.5 N, and preferably between 0.75N and 0.25N, and at room temperature, or preferably difluoroacetic acid dissolved in a mixture of solvents such as an acetonitrile/water (1:1, v/v) mixture when the compound of formula (I) which it is desired to obtain possesses a radical R$_2$ other than a hydrogen atom, to obtain a compound of formula (I/a):

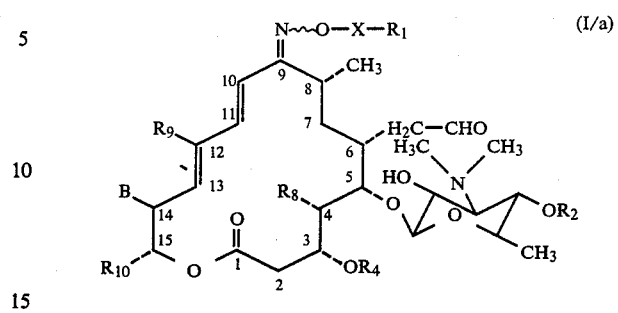

which is a special case of the compounds of formula (I) in which the sign ∼∼, X, R$_1$, R$_2$, R$_4$, R$_8$, R$_9$, R$_{10}$ and B have the same definition as in the formula (I), A in this case denoting an oxygen atom, which compound, in the case where, in the starting material used, R$_2$ does not denote a hydrogen atom, may, during the process of synthesis, depending on the working conditions selected as well as the meanings of the groups X, R$_1$, R$_8$, R$_9$, R$_{10}$ and B, have been partially hydrolyzed to a demycarosylated derivative (I/a) for which R$_2$=H, the two compounds thereby obtained (that is to say, that for which R$_2$=H and that for which R$_2$ corresponds to a mycarosyl residue) then being readily separated by a conventional separation technique such as chromatography on a silica column, it then being possible for this compound of formula (I/a), where appropriate, to be treated in the presence of a base such as, for example, pyridine or triethylamine, or an alkali metal salt such as sodium acetate, potassium hydrogen carbonate or sodium hydrogen carbonate, sodium carbonate or potassium carbonate or calcium carbonate, either with a compound of formula (VII):

$$H_2N—O—Y—R_5 \quad (VII)$$

in which Y and R$_5$ have the same definition as in the formula (I), with the exception of the case in which Y—R$_5$ denotes a hydrogen atom, or with a strong acid salt of such a product, to obtain, after optional purification by chromatography on a silica column, a derivative of formula (I), or with a strong acid salt of hydroxylamine to obtain a product of formula (I/b)

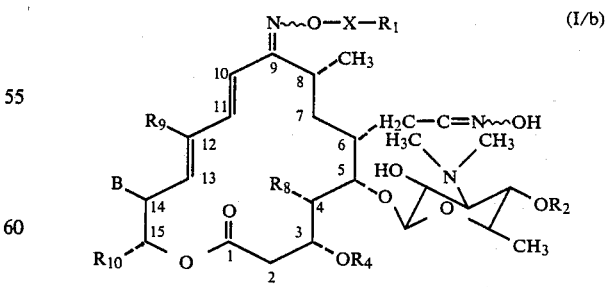

which is a special case of compounds of formula (I) in which the sign ∼∼, X, R$_1$, R$_2$, R$_4$, R$_8$, R$_9$, R$_{10}$ and B have the same meaning as in the formula (I), A in this case denoting a group N∼∼O—Y—R$_5$ in which Y—R$_5$ denotes a hydrogen atom, which is treated, where appropriate, in the presence of a base such as, for example, triethylamine or pyridine, or an alkali metal salt such as sodium carbonate or potassium carbonate or sodium hydrogen carbonate or potassium hydrogen carbonate, or alternatively an alkali metal hydride such as sodium hydride, in a solvent preferably chosen from acetone, dimethylformamide, dioxane, acetonitrile, tetrahydrofuran and diethyl or diisopropyl ether, with a product of formula (VIII):

$$R_5-Y-T' \qquad (VIII)$$

in which T' denotes a halogen atom and $R_5$ and Y have the same meaning as in the formula (I), with the exception of the case in which $R_5$—Y together denote a hydrogen atom, to obtain a compound of formula (I), which is optionally purified by chromatography on a silica column using a suitable solvent mixture such as, for example, a methylene chloride/methanol mixture, and which can, if so desired:

either be salified with a pharmaceutically acceptable acid, or be separated into its isomers and then, if necessary, salified with a pharmaceutically acceptable acid.

The derivatives of formula (V) are new, and form part of the invention on the same basis as the derivatives of formula (I), of which they constitute the synthesis intermediates.

A special case of the present invention relates to the compounds of formula (I) in which A denotes a group of formula:

N~O—Y—R$_5$, Y—R$_5$ having the same meaning as X—R$_1$.

Such compounds may be obtained by a simplified variant of the process stated above, wherein a derivative of formula (II/1a) or (II/2) or (II/2b), depending on the compound of formula (I) which it is desired to obtain:

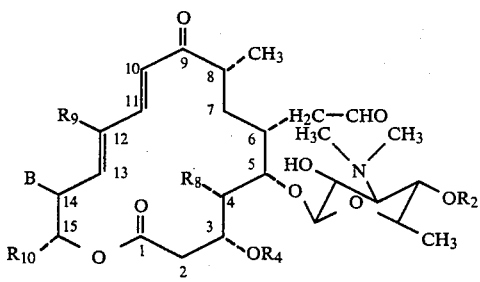

in which $R_2$, $R_4$, $R_8$, $R_9$, $R_{10}$ and B have the same definition as in that stated above for each of the formulae (II/1) or (II/2) or (II/2b), in the presence of a base such as, for example, pyridine or triethylamine, or an alkali metal salt such as sodium acetate or sodium hydrogen carbonate or potassium hydrogen carbonate or sodium carbonate or potassium carbonate or calcium carbonate, is condensed either with a compound of formula (IV):

$$H_2N-O-X-R_1 \qquad (IV)$$

in which X—R$_1$ has the same meaning as in the formula (I) with the exception of the case in which X—R$_1$ denotes a hydrogen atom, to obtain a compound of formula (IX):

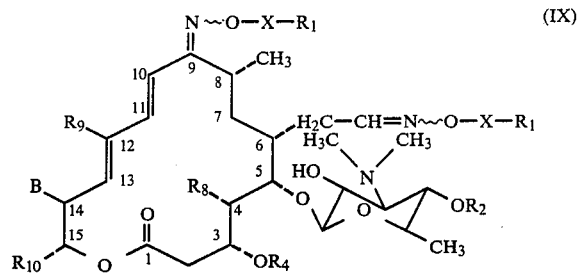

which is a special case of the derivatives of formula (I) in which the sign ~, X, $R_1$, $R_2$, $R_4$, $R_8$, $R_9$, $R_{10}$ and B have the same meaning as in the formula (I), or with a strong acid salt of hydroxylamine to obtain a compound of formula (IX/a):

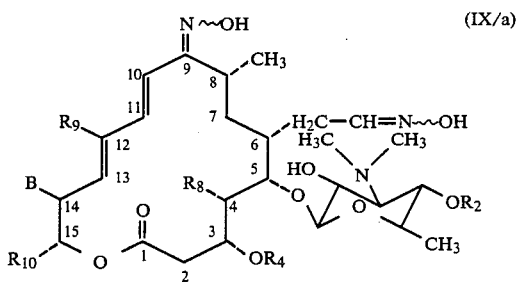

which is a special case of the compounds of formula (I) and (IX), in which the sign ~, $R_2$, $R_4$, $R_8$, $R_9$, $R_{10}$ and B have the same meaning as in the formula (I), X—R$_1$ and Y—R$_5$ in this case together denoting a hydrogen atom, which is optionally treated in the presence of a base such as, for example, triethylamine or pyridine, or an alkali metal salt such as sodium carbonate, potassium carbonate, or sodium hydrogen carbonate or potassium hydrogencarbonate or an alkali metal hydride such as sodium hydride, in a solvent preferably chosen from acetone or dimethylformamide, dioxane, acetonitrile, tetrahydrofuran or diethyl or diisopropyl ether, with a compound of formula (X):

$$R_1-X-T'' \qquad (X)$$

in which T'' denotes a halogen atom and $R_1$ and X have the same meaning as in the formula (I), with the exception of the case in which $R_1$ and X together form a hydrogen atom, to obtain a product of formula (IX), which is a special case of the compounds of formula (I) in which the sign ~, $R_1$, $R_2$, $R_4$, $R_8$, $R_9$, $R_{10}$, B and X have the same meaning as in the formula (I), which is optionally purified by chromatography on a silica column using a suitable solvent mixture such as, for example, a methylene chloride/methanol mixture, and which can, if so desired:

either be salified with a pharmaceutically acceptable acid, or be separated into its isomers and then, if necessary, salified with a pharmaceutically acceptable acid.

The compounds of formula (I) possess advantageous pharmacological properties.

In particular, these compounds are active with respect to Gram+cocci and Gram−cocci, Gram+bacillae (clostridia), some Gram—bacillae, Haemophilus (e.g. Haemophilus influenzae), Nesseiria gonorhoeae, Brucella, Bordetella, anaerobic bacteria, mycoplasms, rickettsiae and Miyagawanella (Chlamydia), spirochetes, protozoa and some dermofungi.

More especially, the compounds of formula (I) possess very good antibiotic activity with respect to pneumococci, staphylococci and streptococci. This spectrum of activity makes the compounds of formula (I) especially advantageous in the treatment of a large number of conditions; among the latter, it is possible to mention, by way of example, pneumonococcoses such as bronchitis, brucellosis, diphtheria, gonococcosis, pneumonia, streptococcoses such as acute throat infections, otitis, scarlet fever, sinusitis, staphylococcoses such as staphylococcal septicemia, anthrax, erysipelas, pyroderma, acute staphylococcoses, broncopneumonia and pulmonary suppurations.

In addition, the compounds of the present invention, as a result of their structure, are likely to prove advantageous on account of their absence of hepatic or gastrointestinal toxicity, which distinguishes them advantageously from other families of antibiotic compounds.

The subject of the present invention is also the pharmaceutical compositions containing the products of formula (I), or one of their addition salts with a pharmaceutically acceptable acid, alone or in combination with one or more pharmaceutically acceptable, nontoxic inert vehicles or excipients.

Among the pharmaceutical compositions according to the invention, there may be mentioned, more especially, those which are suitable for oral, parenteral, nasal, rectal, perlingual, ocular or respiratory administration, and in particular injectable preparations or preparations to be taken by mouth, aerosols, eye or nose drops, simple or sugar-coated tablets, sublingual tablets, sachets, packets, sublingual formulations, pills, suppositories, creams, ointments, skin gels, and the like.

The pharmaceutical compositions according to the invention can also take the form of a lyophilized powder which is intended to be dissolved at the time of use in a suitable solvent, in particular pyrogen-free sterile water.

The appropriate dosage varies according to the patient's age and weight, the administration route and the nature of the therapeutic indication and of possible associated treatments, and ranges between 1 centigram and 4 grams per dose or per application.

The examples which follow illustrate the invention and in no way limit the latter.

The $^{13}C$ and $^{1}H$ nuclear magnetic resonance spectra were recorded using TMS as internal reference.

The starting materials used in the synthesis of the compound of formula (I) are tylosin or josamycin, which are known in the literature.

EXAMPLE 1: DEMYCAROSYLTYLOSIN (E+Z)-9-OXIME

STAGE A: Demycarosyltylosin 20-(diethyl acetal)

907 mg (0.001 mmol) of tylosin base are dissolved in anhydrous ethanol (8.3 ml) and 260 mg (1.5 mmol) of anhydrous p-toluenesulfonic acid are then added at room temperature. The mixture is stirred for 2 hours and 0.2 ml of triethylamine is then added. Stirring is maintained for a further 10 minutes, and half the solvent is then evaporated under reduced pressure. The residue is extracted with dichloromethane and the extract then washed with saturated sodium bicarbonate solution (2×30 ml) and water (2×30 ml). The organic phase is dried over sodium sulfate and then evaporated to dryness. A crude residue (1.150 g) is obtained, which is chromatographed (flash chromatography) using the system $CH_2Cl_2$: $MeOH + 100:4$. The demycarosyltylosin 20-(diethyl acetal) (750 mg; 88%) thereby obtained appears to be chromatographically pure.

Spectral characteristics:

$^{13}C$ NMR 203.6 ppm : $C(C=O)$ (carbon$^9$)

Mass spectrometry:

$[M-H]^+$:M/Z :846

STAGE B: Demycarosyltylosin 20-(diethyl acetal) (E+Z)-9-oxime 950 mg (1.12 mmol) of demycarosyltylosin 20-(diethyl acetal), obtained in Stage A, are dissolved in 30 ml of anhydrous pyridine. 330 mg (4.74 mmol) of hydroxylamine hydrochloride are added and the mixture is brought to 80° C. for 4 hours. The mixture is diluted in water and then extracted with dichloromethane, and the extract is washed and dried as described in the preceding stage. The crude residue (1.28 g) obtained is purified by flash chromatography ($CH_2Cl_2$: $MeOH=100:3$), thereby enabling the stereochemically pure expected product to be separated from a mixture of its two (Z) and (E) isomers.

Spectral characteristics:

$^{13}C$ NMR (stereochemically pure product)

161.0 ppm: C $(C=N)$ (carbon$^9$)

Mass spectrometry:

$[M-H]^+$:M/Z:861

STAGE C: Demycarosyltylosin (E+Z)-9-oxime 600 mg (0.07 mmol) of stereochemically pure demycarosyltylosin 20-(diethyl acetal) (E+Z)-9-oxime, obtained above, are dissolved in 40 ml of acetonitrile. 40 ml of 0.1N aqueous hydrochloric acid solution are added and the mixture is stirred for 4 hours at room temperature. 20 ml of 5% strength sodium bicarbonate solution are then added, the mixture is extracted with dichloromethane and the extract is washed and dried as described in Stage A. The product obtained is pure.

If a mixture of (Z) and (E) isomers of demycarosyltylosin 20-(diethyl acetal) 9-oxime is used as the starting material, a mixture of (Z) and (E) isomers of demycarosyltylosin 9-oxime is obtained.

Spectral characteristics:

$^{13}C$ NMR 159.8 ppm and 156.7 ppm: signals characteristic of carbon$^9$ for each of the two (Z) and (E) isomers.

Mass spectrometry:

$[M-H]^+$:M/Z:787

Melting point: 136°-137° C.

EXAMPLE 2: TYLOSIN (E+Z)-9,20-DIOXIME 1.8 g (1.96 mmol) of tylosin base are dissolved in 35 ml of anhydrous pyridine and 1.35 g (19 mmol) of hydroxylamine hydrochloride are then added. The mixture is stirred for 4 hours while a temperature of 80° C. is maintained. The reaction medium is diluted with water and extracted with dichloromethane and the extract is then washed with saturated sodium bicarbonate solution (2×30 ml) and then with water (2×30 ml). The organic phase is dried over sodium sulfate and then evaporated to dryness. A crude residue (1.6 g) is obtained, which is purified by chromatography on a silica column using an ethyl acetate/methanol (95:5) mixture (Rf=0.6).

Spectral characteristics:
$^{13}$C NMR
176.1 ppm, 171.5 ppm and 160.3 ppm: peaks characteristic of carbons[1, 9, 20]
Mass spectrometry:
[M—H]$^+$:M/Z:946
Melting point: 140°–148° C.

EXAMPLE 3: DEMYCAROSYLTYLOSIN (E+Z)-9,20-DIOXIME

By the procedure used in Example 2, a mixture of tylosin (E+Z)-9,20-dioxime and demycarosyltylosin (E+Z)-9,20-dioxime is, in fact, obtained, separation of these two compounds being carried out by column chromatography with a 95:5 ethyl acetate/methanol mixture; demycarosyltylosin (E+Z)-9,20-dioxime has an Rf of 0.3.

Spectral characteristics:
$^{13}$C NMR
147.9, 171.0 and 159.5 ppm: peaks characteristic of carbons[1, 9, 20]
Mass spectrometry:
[M—H]$^+$:M/Z:802
Melting point: 128°–134° C.

EXAMPLE 4: DEMYCAROSYTYLOSIN (E+Z)-9-(0-METHYLOXIME)

STAGE A: Demycarosyltylosin 20-(diethyl acetal) (E+Z)-9-(0-methyloxime)

950 mg (1.12 mmol) of demycarosyltylosin 20-(diethyl acetal), obtained in Example 1 Stage A, are dissolved in 30 ml of anhydrous pyridine. 235 mg (2.80 mmol) of methoxyamine hydrochloride are added and the mixture is stirred under a nitrogen atmosphere at room temperature for 48 hours. One volume of ice-cold water is added. The mixture is stirred for a few minutes and extracted with dichloromethane, and the extract is then washed with saturated sodium bicarbonate solution (2×30 ml) and then with water (2×30 ml). The organic phase is dried over sodium sulfate and then evaporated to dryness. A crude residue is obtained, which is purified by chromatography on a silica column using the system $CH_2Cl_2/CH_3OH$ 90:10. The product obtained is used without further treatment in the following stage.

STAGE B: Demycarosyltylosin (E+Z)-9-(0-methyloxime)

The procedure is as in Example 1, Stage C, demycarosyltylosin 20-(diethyl acetal) (E+Z)-9-oxime being replaced by demycarosyltylosin 20-(diethyl acetal) (E+Z)-9-(0-methyloxime).

Spectral characteristics:
$^{13}$C NMR
159.83 and 156.28 ppm: signals characteristic of carbon[9] for each of the (Z) and (E) isomers.
Mass spectrometry:
[M—H]$^+$:M/Z:801

EXAMPLE 5: DEMYCAROSYLTYLOSIN (E+Z)-9-(0-BENZYLOXIME)

STAGE A: Demycarosyltylosin 20-(diethyl acetal) (E+Z)-9-(0-benzyloxime)

2.31 g (2.73 mmol) of demycarosyltylosin 20-(diethyl acetal), obtained in Example 1, Stage A, are dissolved in 40 ml of anhydrous pyridine. 1.7 g (10.92 mmol) of benzyloxyamine hydrochloride are added and the mixture is stirred under a nitrogen atmosphere at room temperature for 96 hours, the progress of the reaction being monitored by thin layer chromatography (solvent mixture $CH_2Cl_2$/MeOH - 9:1 v/v). After the starting material has disappeared, the mixture is extracted with dichloromethane and the extract washed with saturated sodium bicarbonate solution (2×30 ml) and then with water (2×30 ml). The organic phases are combined, dried over sodium sulfate and then evaporated to dryness. A residue is obtained, which is purified by chromatography on a silica column using a dichloromethane/methanol (100:3) mixture and then increasing quantities of methanol.

STAGE B: Demycarosyltylosin (E+Z)-9-(0-benzyloxime)

By the procedure used in Example 1, Stage C, but demycarosyltylosin 20-(diethyl acetal) (E+Z)-9-oxime being replaced by demycarosyltylosin 20-(diethyl acetal) (E+Z)-9-(0-benzyloxime), obtained in the preceding stage, demycarosyltylosin (E+Z)-9-(0-benzyloxime) is obtained.

Spectral characteristics:
Nuclear magnetic resonance, $^1$H NMR, 400 MHz
δ=7.35 to 7.50 ppm, complex, 5H, aromatic.
Mass spectrometry:
[M—H]$^+$:M/Z:877

EXAMPLE 6: TYLOSIN (E+Z)-9-(0-BENZYLOXIME)

STAGE A: Tylosin 20-(dimethyl acetal)

6.0 g (65 mmol) of tylosin base are dissolved in 60 ml of anhydrous methanol and 4.1 ml (6.5 mmol) of difluoroacetic acid are then added. The mixture is stirred at room temperature for 120 hours. 9 ml (65 mmol) of triethylamine are added and the mixture is stirred for 1 hour at room temperature. The methanol is evaporated off to dryness. 150 ml of dichloromethane are added and the mixture is then washed with water. The organic phase is dried over sodium sulfate and then evaporated to dryness. A crude residue is obtained, which is chromatographed (flash chromatography) using the system $CH_2Cl_2$/MeOH/$NH_4OH$ (20:1:0.05). The tylosin 20-(dimethyl acetal) (2.6 g; 41.6%) thereby obtained appears to be chromatographically pure.

STAGE B: Tylosin 20-(dimethyl acetal) O-benzyloxime 2.6 g (2.7 mmol) of tylosin 20-(dimethyl acetal), obtained in Stage A, are dissolved in 20 ml of anhydrous pyridine. 1.68 g (10.8 mmol) of benzyloxyamine hydrochloride are added and the mixture is stirred at room temperature for 72 hours. One volume of ice-cold water is added. The mixture is stirred for a few minutes and extracted with dichloromethane (3×50 ml). The organic phase is evaporated to dryness. A crude residue is obtained, which is purified by chromatography as described in Stage A. 1.95 g of chromatographically pure product are obtained.
Yield: 70%

STAGE C: Tylosin O-benzyloxime 1.5 g (1.4 mmol) of tylosin 20-(dimethyl acetal) O-benzyloxime, obtained above, are dissolved in 100 ml of an acetonitrile/water (1:1) mixture. 0.46 ml (7 mmol) of difluoroacetic acid is added and the mixture is stirred at room temperature for 37 hours. 0.95 ml of triethylamine is added and the mixture is stirred for 1 hour. The acetonitrile is evaporated off and the residue extracted with dichloromethane (3×80 ml). The organic phase is dried over sodium sulfate and then evaporated to dryness. The crude residue (3 g) is obtained, which is purified by chromatography as described in Stage A. Pure tylosin O-benzyloxime is obtained.

Yield: 30%

If a mixture of (Z) and (E) isomers of tylosin 20-(dimethyl acetal) is used as the starting material, a mixture of (Z) and (E) isomers of tylosin O-benzyloxime is obtained.

Spectral characteristics:
$^1$H NMR 200 MHz (ppm)
$\delta$=2.45 ppm, singlet, 6H (2×CH$_3$):N(CH$_3$)$_2$
$\delta$=5.00 ppm, singlet, 2H, CH$_2$(O-CH$_2$-C$_6$H$_5$)
$\delta$=7.20 ppm, complex, 5H, aromatic
$\delta$=9.40 ppm, complex, resolvable, 1 H, aldehyde
Mass spectrometry:
[M—H]$^+$:M/Z:1021

EXAMPLE 7:
9-{(E+Z)-0-[(2-METHOXYETHOXY)METHYL]-OXYIMINO}-9-DEOXYTYLOSIN

STAGE A: Tylosing 20-(dimethyl acetal) (E+Z)-9-oxime 2.0 g (2.08 mmol) of tylosin 20-(dimethyl acetal), obtained in Example 6, Stage A, are dissolved in 5 ml of anhydrous pyridine. 0.433 g (2.08 mmol) of hydroxylamine hydrochloride is added and the mixture is stirred at room temperature for 12 hours. One volume of ice-cold water is added. The mixture is stirred for a few minutes and extracted with ethyl acetate (3×50 ml). The organic phase is dried over sodium sulfate and then evaporated to dryness. 1.6 g (80%) of product are obtained, the purity of which is monitored by chromatography on a silica column using a mixture CH$_2$Cl$_2$/MeOH/NH$_4$OH=10:1:0.5.

STAGE B:
9-{(E+Z)-0-[(2-Methoxyethoxy)methyl]-oxyimino}-9-deoxytylosin 20-(dimethyl acetal)

0.51 g (0.52 mmol) of tylosin 20-(dimethyl acetal) (E+Z)-9-oxime, obtained in Stage A, is dissolved in 10 ml of anhydrous tetrahydrofuran. 27 mg of a 50% strength suspension in oil of the sodium hydride (0.57 mmol) are added and the mixture is stirred at room temperature for 15 minutes. 64 μl (0.62 mmol) of (methoxyethoxy)methyl chloride are added and the mixture is stirred at room temperature for 30 minutes. After the addition of 50 mg of magnesium trisilicate, tetrahydrofuran is evaporated off to dryness. 200 ml of dichloromethane are added and the mixture is filtered. The organic phase is evaporated to dryness and purified by flash chromatography (CH$_2$Cl$_2$/MeOH/ NH$_4$OH-20:1:0.5). Chromatographically pure 9-{(E+Z) -0-[(2-methoxyethoxy)methyl]-oxyimino}-9-deoxytylosin 20-(dimethyl acetal) is obtained.

Yield: 55%

STAGE C:
9-{[(E+Z)-0-[(2-Methoxyethoxy)methyl]-oxyimino}-9-deoxytylosin 0.28 g (2.6 mmol) of 9-{[(E+Z)-0-[(2-methoxyethoxy) -methyl]-oxyimino}-9-deoxytylosin 20-(dimethyl acetal), obtained above, is dissolved in 20 ml of an acetonitrile/water (1:1) solvent mixture. 82 μl (13 mmol) of trifluoroacetic acid are added and the mixture is stirred for 37 hours at room temperature. 50 μl (2.6 mmol) of triethylamine are added and the mixture is stirred for 1 hour. The acetonitrile is evaporated off and the residue extracted with dichloromethane (3×30 ml). The organic phase is dried over sodium sulfate and then evaporated to dryness. A crude residue is obtained, which is purified and separated from the demycarosylated derivative by flash chromatography as described in Stage B. 9-{[(E+Z)-0-[(2-Methoxyethoxy) methyl]oxyimino}-9-deoxytylosin is obtained.

Yield: 28%

Spectral characteristics:
$^1$H NMR 200 MHz $\delta$ (ppm)
$\delta$=2.50 ppm, singlet, 6H(2×CH$_3$) : N-(CH$_3$)$_2$
$\delta$=3.36 ppm, singlet, 3H (CH$_3$) (OCH$_2$-O(CH$_2$)$_2$-)CH$_3$
$\delta$=9.70 ppm, singlet, 1H, (CH=O)
Mass spectrometry:
[M—H]$^+$:M/Z:1019

EXAMPLE 8:
9-{(E+Z)-0-[(2-METHOXYETHOXY)METHYL]-OXYIMINO}-9-DEOXYDEMYCAROSYL-TYLOSIN

During the purification of the crude residue obtained in the same manner as in Example 7, Stage C, after separation of the mycarosylated derivative by flash chromatography, 9-{(E=Z)-0-[(2-methoxyethoxy)methyl]oxyimino}9-deoxydemycarosyltylosin is obtained.

Yield: 40%

Spectral characteristics:
$^1$H NMR 200 MHz $\delta$ (ppm)
$\delta$=2.45 ppm, singlet, 6H(2×CH$_3$):N-(CH$_3$)$_2$
$\delta$=3.35 ppm, singlet, 3H (CH$_3$) (OCH$_2$-O(CH$_2$)$_2$-OCH$_3$)
$\delta$=9.80 ppm, singlet, 1H, (CH=O)
Mass spectrometry:
[M—H]$^+$:M/Z:875

EXAMPLES 9 AND 10:

In the same manner as in Example 5, benzyloxylamine hydrochloride being replaced by:
O-allylhydroxylamine hydrochloride (EXAMPLE 9),
O-ethylhydroxylamine hydrochloride (EXAMPLE 10), the following are obtained:

EXAMPLE 9:
9-[(E+Z)-ALLYLOXYIMINO]-9-DEOXYDEMYCAROSYLTYLOSIN

EXAMPLE 10:
9-[(E+Z)-ETHYLOXYIMINO]-9-DEOXYDEMYCAROSYLTYLOSIN

EXAMPLE 11:
9-[(E+Z)-ALLYLOXYIMINO]-9-DEOXYTYLOSIN

By the same procedure as that used in Example 6, but benzyloxyamine hydrochloride in Stage B being replaced by allylhydroxylamine hydrochloride, the expected product is obtained.

EXAMPLE 12:
9-[(E+Z)ETHYLOXYIMINO]-9-DEOXYTYLOSIN

By the same procedure as that using Example 6, but benzyloxyamine hydrochloride in Stage B being replaced by O-ethylhydroxylamine hydrochloride, the expected product is obtained.

EXAMPLE 13 AND 14:
9-{(E+Z)-0-[2-(VINYLOXY)ETHYL]OXYIMINO}-9-DEOXYTYLOSIN AND
9-{(E+Z)-0-[2-(VINYLOXY)ETHYL]OXYIMINO}-9-DEOXYDEMYCAROSYLTYLOSIN

By the procedure used in Examples 7 and 8, but (2-methoxyethoxy)methyl chloride in Stage B being replaced by 2-chloro-1-(vinyloxy)ethane, the expected products are obtained.

EXAMPLE 15: TYLOSIN (E+Z)-9-[0-(2-DIMETHYLAMINOETHYL)OXIME

The procedure used is as in Example 7, (2-methoxyethoxy) methyl chloride in Stage B being replaced by twice the quantity of 1-chloro-2-dimethylaminoethane hydrochloride.

EXAMPLE 16: DEMYCAROSYLTYLOSIN (E+Z)-9-[0-(2-DIMETHYLAMINOETHYL)OXIME

During final purification of the compound of Example 15, the expected compound is obtained.
Spectral characteristics:
Mass spectrometry:
[M—H]+:M/Z:857

EXAMPLES 17 AND 18:
9-[(E+Z)-(2-DIMETHYLAMINO-1-METHYLETHYL)OXYIMINO]-9-DEOXYTYLOSIN AND
9-[(E+Z)-(2-DIMETHYLAMINO-1-METHYLETHYL)OXYIMINO]-9-DEOXYDEMYCAROSYLTYLOSIN

By the procedure used in Examples 15 and 16, but 1-chloro-2-dimethylaminoethane hydrochloride being replaced by 2-chloro-1-dimethylaminopropane hydrochloride, the two products in the title are obtained.

EXAMPLE 19:
9-{(E+Z)-[2-(4-MORPHOLINYL)ETHYL]-OXYIMINO}-9-DEOXYTYLOSIN

By the procedure used in Example 7, but (2-methoxyethoxy) methyl chloride being replaced by 4-(2-chloroethyl)morpholine hydrochloride, the expected product is obtained.

EXAMPLE 20:
9-{(E+Z)-[2-(4-MORPHOLINYL)ETHYL]OXYIMINO}-9-DEOXYDEMYCAROSYLTYLOSIN

During the final purification of the compound of Example 19, the expected compound is obtained.

EXAMPLES 21 AND 22:
9-{(E+Z)-[2-(1-PYRROLIDINYL)ETHYL]OXYIMINO}-9-DEOXYTYLOSIN AND
9-{(E+Z)-[2-(1-PYRROLIDINYL)ETHYL]OXYIMINO-9-DEOXYDEMYCAROSYLTYLOSIN

By the replacement of 4-(2-chloroethyl)morpholine hydrochloride in Examples 19 and 20 by 1-(2-chloroethyl) pyrrolidine hydrochloride, the expected products are obtained.

EXAMPLES 23 AND 24:
9-{(E+Z)-[2-(1-PIPERIDYL)-ETHYL]OXYIMINO}-9-DEOXYTYLOSIN AND
9-{(E+Z)-[2-(1-PIPERIDYL)-ETHYL]OXYIMINO}-9-DEOXYDEMYCAROSYLTYLOSIN

By the replacement of 4-(2-chloroethyl)morpholine hydrochloride in Examples 19 and 20 by 1-(2-chloroethyl) piperidine, the expected products are obtained.

EXAMPLES 25 and 26:
Tylosin 9,20-bis[(E+Z)-0-methyloxime]
Demycarosyltylosin 9,20-bis[(E+Z)-0-methyloxime]

By the procedure used in Examples 2 and 3, but hydroxylamine hydrochloride being replaced by O-methylhydroxylamine hydrochloride, the following are obtained:

EXAMPLE 25: TYLOSIN 9,20-BIS[(E+Z)-O-METHYLOXIME]

EXAMPLE 26: DEMYCAROSYLTYLOSIN 9,20-BIS[(E+Z)-O-METHYLOXIME]

EXAMPLE 27: TYLOSIN 9,20-BIS[O-(20METHOXYETHOXY)-METHYLOXIME]

2.2 g (2.32 mmol) of tylosin (E+Z)-9,20-dioxime are dissolved in 40 cm$^3$ of tetrahydrofuran. 236 mg (5 mmol) of a 50% strength suspension in oil of sodium hydride are added, and the mixture is stirred at room temperature for 15 minutes. 0.6 g (4.8 mmol) of (2-methoxyethoxy)methyl chloride is added and the mixture is stirred at room temperature for 2 hours. After the addition of 500 mg of magnesium trisilicate, the tetrahydrofuran is evaporated off the dryness. 300 ml of dichloromethane are added and the mixture is filtered. The organic phase is evaporated to dryness and purified by chromatography on silica gel.
Spectral characteristics:
Mass spectrometry:
[M—H]+:M/Z:1122

EXAMPLE 28: DEMYCAROSYLDEMYCINOSYLTYLOSIN (E+Z)-9-OXIME

STAGE A: Demycarosyltylosin 4 g (0.004 mmol) of tylosin base are stirred in 80 ml of 0.2N hydrochloric acid for 4 hours at room temperature. The reaction medium obtained is washed with dichloromethane and the aqueous phase is separated and adjusted to pH 8.0. The latter phase is extracted twice with 120 ml of dichloromethane, and the organic phases are combined, dried over sodium sulfate and evaporated. The residue consists of demycarosyltylosin.
Yield: 94%
Spectral characteristics:
Mass spectrometry:
[M—H]+:M/Z:772

STAGE B: Demycarosyldemycinosyltylosin 5 g (0.0065 mmol) of demycarosyltylosin, obtained in Stage A, are dissolved in 110 ml of 0.5N hydrochloric acid and the mixture is stirred for approximately 27 hours at 75° C. The reaction medium is washed with dichloromethane. The aqueous phase is recovered, adjusted to pH 8 and extracted twice with 120 ml of dichloromethane. The organic phase is dried over sodium sulfate and evaporated. The residue is chromatographed on silica gel (eluant: CH$_2$Cl$_2$/MeOH/NH$_4$OH 10:1:0.5) to obtain the expected product.

Yield: 20%
Spectral characteristics:
Mass spectrometry:
[M—H]$^+$:M/Z:598

STAGE C: Demycarosyldemycinosyltylosin 20-(diethyl acetal)

540 mg (0.9 mmol) of demycarosyldemycinosyltylosin are dissolved in 10 ml of anhydrous ethanol. 400 mg of anhydrous p-toluenesulfonic acid are added at room temperature. The mixture is stirred for 4 hours at room temperature and 0.3 ml of triethylamine is added. Stirring is maintained for a further 10 minutes and half the solvent is evaporated off under reduced pressure. The residue is diluted with water, extracted with dichloromethane, and washed twice with 30 ml of sodium bicarbonate solution and then twice with 30 ml of water. The organic phase is dried over sodium sulfate and evaporated to dryness. The expected product is obtained.

Yield: 80%
Spectral characteristics:
Mass spectrometry:
[M—H]$^+$:M/Z:672

STAGE D: Demycarosyldemycinosyltylosin 20-(diethyl acetal) (E+Z)-9-oxime 100 mg (0.15 mmol) of demycarosyldemycinosyltylosin 20-(diethyl acetal), obtained in Stage C, are dissolved in 4.5 ml of anhydrous pyridine. 45 mg (0.65 mmol) of hydroxylamine hydrochloride are added and the mixture is brought to 80° C. for 4 hours. The mixture is diluted in water and then extracted with dichloromethane, and the extract is washed and dried as described in the preceding stage. The crude residue obtained is purified by flash chromatography.

Spectral characteristics:
Mass spectrometry:
[M—H]$^+$:M/Z:687

STAGE E: Demycarosyldemycinosyltylosin (E+Z)-9-oxime 500 mg (0.73 mmol) of demycarosyldemycinosyltylosin 20-(diethyl acetal) (E+Z)-9-oxime, obtained above, are dissolved in 40 ml of acetonitrile. 40 ml of 0.2N aqueous hydrochloric acid solution are added and the mixture is stirred for 4 h 30 min at room temperature. 20 ml of 5% strength sodium bicarbonate solution are then added, the mixture is extracted with dichloromethane and the extract is washed and dried as described in Stage C. The product obtained is purified by preparative chromatography.

Spectral characteristics:
Mass spectrometry:
[M—H]$^+$:M/Z:613

EXAMPLE 29: DEMYCAROSYLDEMYCINOSYLTYLOSIN (E+Z)-9,20-DIOXIME 250 mg (0.42 mmol) of demycarosyldemycinosyltylosin base, obtained in Example 1, Stage B, are dissolved in 30 ml of anhydrous pyridine and 0.30 g (4.3 mmol) of hydroxylamine hydrochloride is then added. The mixture is stirred for 4 hours while a temperature of 80° C. is maintained. The reaction medium is diluted with water and extracted with dichloromethane, and the extract is then washed with saturated sodium bicarbonate solution (2×10 ml) and then with water (2×10 ml). The organic phase is dried over sodium sulfate and then evaporated to dryness. A crude residue is obtained, which is purified by chromatography on a silica column.

Spectral characteristics:
Mass spectrometry:
[M—H]$^+$:M/Z:628

EXAMPLE 30: DEMYCAROSYLDEMYCINOSYLTYLOSIN (E+Z)-9-(O-METHYLOXIME)

STAGE A: Demycarosyldemycinosyltylosin 20-(diethyl acetal) (E+Z)-9-(O-methyloxime)

100 mg (0.15 mmol) of demycarosyldemycinosyltylosin 20-(diethyl acetal), obtained in Example 28, Stage C, are dissolved in 4.5 ml of anhydrous pyridine. 33 mg (0.40 mmol) of methoxylamine hydrochloride are added, and the mixture is stirred under a nitrogen atmosphere at room temperature for 48 hours. One volume of ice-cold water is added. The mixture is stirred for a few minutes and extracted with dichloromethane, and the extract is washed with saturated sodium bicarbonate solution (2×30 ml) and then with water (2×30 ml). The organic phase is dried over sodium sulfate and then evaporated to dryness. A crude residue is obtained, which is purified by chromatography on a silica column. The product obtained is used without further treatment in the following stage.

STAGE B: Demycarosyldemycinosyltylosin (E+Z)-9-(O-methyloxime)

The procedure used is as in Example 28, Stage E, demycarosyldemycinosyltylosin 20-(diethyl acetal) (E+Z)-9-oxime being replaced by demycarosyldemycinosyltylosin 20-(diethyl acetal) (E+Z)-9-(O-methyloxime).

Spectral characteristics:
Mass spectrometry:
[M—H]$^+$:M/Z:627

EXAMPLE 31: DEMYCAROSYLDEMYCINOSYLTYLOSIN (E+Z)-9-(O-BENZYLOXIME)

STAGE A: Demycarosyldemycinosyltylosin 20-(diethyl acetal) (E+Z)-9-(O-benzyloxime)

100 mg (0.15 mmol) of demycarosyldemycinosyltylosin 20-(diethyl acetal), obtained in Example 28, Stage C, are dissolved in 4.5 ml of anhydrous pyridine. 96 mg (0.6 mmol) of benzyloxyamine hydrochloride are added and the mixture is stirred under a nitrogen atmosphere at room temperature for 72 hours. The mixture is extracted with dichloromethane and the extract washed with saturated sodium bicarbonate solution (2×30 ml) and then with water (2×30 ml). The organic phases are combined, dried over sodium sulfate and then evaporated to dryness. A residue is obtained, which is purified by chromatography on a silica column using a dichloromethane/methanol/ammmonia (20:1:0.05) mixture as elution solvent.

Yield: 80%
Spectral characteristics:
Mass spectrometry:
[M—H]$^+$:M/Z:777

STAGE B: Demycarosyldemycinosyltylosin (E+Z) -9-(O-benzyloxime)

By the procedure used in Example 28, Stage E, but demycarosyldemycinosyltylosin 20-(diethyl acetal) (E+Z)- 9-oxime being replaced by demycarosyldemycinosyltylosin 20-(diethyl acetal) (E+Z)-9-(O-benzyloxime) obtained in the preceding stage, demycarosyldemycinosyltylosin (E+Z) -9-(O-benzyloxime) is obtained, which is purified by preparative chromatography (elution solvent: dichloromethane/methanol/ammonia 10:1:0.05).

$^1$H Nuclear magnetic resonance spectrometry (400 MHz):
δ=0.96 ppm 3H, $CH_3$, $C_{17}$
δ=1.00 ppm 3H, $CH_3$, $C_{18}$
δ=5.12 ppm, $CH_2$, $CH_2$—$C_6H_5$
δ=7.38 ppm aromatic
Spectral characteristics:
Mass spectrometry:
[M—H]$^+$:M/Z:703

EXAMPLES 32 AND 33:

In the same manner as in Example 31, benzyloxyamine hydrochloride being replaced by:
O-allylhydroxylamine hydrochloride (EXAMPLE 32),
O-ethylhydroxylamine hydrochloride (EXAMPLE 33), the following are obtained:

EXAMPLE 32:
DEMYCAROSYLDEMYCINOSYLTYLOSIN (E+Z) -9-(O-ALLYLOXIME)

EXAMPLE 33:
DEMYCAROSYLDEMYCINOSYLTYLOSIN (E+Z) -9-(O-ETHYLOXIME)

EXAMPLE 34:
9-{O-[(2-METHOXYETHOXY)METHYL]OXYIMINO}-9-DEOXYDEMYCAROSYL-DEMYCINOSYLTYLOSIN 2 g (2.92 mmol) of demycarosyldemycinosyltylosin 20-(diethyl acetal) (E+Z)-9-oxime (obtained in Stage D of Example 28, are dissolved in tetrahydrofuran, and the procedure is than an in Example 7, Stage B; 9-{(E+Z)-O -[(2-methoxyethoxy)methyl]oxyimino}-9-deoxydemycarosyldemycinosyltylosin 20-(diethyl acetal) is obtained, which is then dissolved in 40 ml of acetonitrile and treated according to the protocol detailed in Example 28, Stage E.
Spectral characteristics:
Mass spectrometry:
[M—H]$^+$:M/Z:701

EXAMPLE 35:
DEMYCAROSYLDEMYCINOSYLTYLOSIN (E+Z) -9-{O-[2-(VINYLOXY)ETHYL]OXIME}

By the procedure used in the preceding example, but (2-methoxyethoxy)methyl chloride being replaced by 2-chloro-1-(vinyloxy)ethane, the expected product is obtained.
Spectral characteristics:
Mass spectrometry:
[M—H]$^+$:M/Z:683

EXAMPLE 36:
DEMYCAROSYLDEMYCINOSYLTYLOSIN (E+Z) -9-[O-(2-DIMETHYLAMINOETHYL)OXIME]

1.8 g (2.94 mmol) of demycarosyldemycinosyltylosin 20-(dimethyl acetal) (E+Z)-9-oxime, obtained in Example 28, Stage D, are dissolved in 50 cm$^3$ of tetrahydrofuran. 142 mg (3 mmol) of a 50% strength suspension in oil of sodium hydride are added, and the mixture is stirred at room temperature for 15 minutes. 0.44 g (3 mmol) of 1-chloro-2-dimethylaminoethane hydrochloride is added and the mixture is stirred at room temperature for 1 hour. After the addition of 300 mg of magnesium silicate, the tetrahydrofuran is evaporated off. 200 ml of dichloromethane are added and the mixture is filtered and evaporated to dryness. The residue is purified by chromatography on a silica column and then dissolved in 150 ml of acetonitrile. 150 ml of 0.2N aqueous hydrochloric acid solution are added and the mixture is stirred for 4 h 30 min at room temperature. 20 ml of 5% strength sodium bicarbonate solution are then added and the mixture is extracted with dichloromethane. The extract is washed and dried and the product purified by chromatography on a silica column.
Spectral characteristics:
Mass spectrometry:
[M—H]$^+$:M/Z:684

EXAMPLE 37:
DEMYCAROSYLDEMYCINOSYLTYLOSIN (E+Z) -9[O-(2-DIMETHYLAMINO-1-METHYLETHYL) -OXIME]

By the procedure used in Example 36, but 1-chloro -2-dimethylaminoethane hydrochloride being replaced by 2-chloro-1-dimethylaminopropane hydrochloride, demycarosyldemycinosyltylosin (E+Z)-9-[O-(2-dimethylamino-1-methylethyl) oxime] is obtained.
Spectral characteristics:
Mass spectrometry:
[M—H]$^+$:M/Z:698

EXAMPLE 38:
DEMYCAROSYLDEMYCINOSYLTYLOSIN (E+Z) -9-{O-[2-(4-MORPHOLINYL)ETHYL]OXIME}

1.8 g (2.94 mmol) of demycarosyldemycinosyltylosin 20-(dimethyl acetal) (E+Z)-9-oxime, obtained in Example 28, are dissolved in 50 cm$^3$ of tetrahydrofuran, and the procedure is then as in the preceding example, 1-chloro -2-dimethylaminoethane hydrochloride being replaced by 4-(2-chloroethyl)morpholine hydrochloride.
Spectral characteristics:
Mass spectrometry:
[M—H]$^+$:M/Z:726

EXAMPLE 39:
DEMYCAROSYLDEMYCINOSYLTYLOSIN (E+Z) -9-{O-[2-(1-PYRROLIDINYL)ETHYL]OXIME}

By the replacement of 4-(2-chloroethyl)morpholine hydrochloride in the preceding example by 1-(2-chloroethyl)pyrrolidine, the expected product is obtained
Spectral characteristics:
Mass spectrometry:
[M—H]$^+$:M/Z:710

EXAMPLE 40: DEMYCAROSYLDEMYCINOSYLTYLOSIN (E+Z) -9{O-[2-(1-PIPERIDYL)ETHYL]OXIME}

By the replacement of 4-(2-chloroethyl)morpholine hydrochloride by 1-(2-chloroethyl)piperidine hydrochloride, the expected product is obtained.
Spectral characteristics:
Mass spectrometry:
[M—H]+:M/Z:724

EXAMPLE 41: DEMYCAROSYLDEMYCINOSYLTYLOSIN 9,20-BIS[(E+Z)-O-METHYLOXIME]

By the procedure used in Example 29, but hydroxylamine hydrochloride being replaced by O-methylhydroxylamine hydrochloride, the expected product is obtained.
Spectral characteristics:
Mass spectrometry
[M—H]+ : M/Z :656

EXAMPLE 42: DEMYCAROSYLDEMYCINOSYLTYLOSIN 9,20-BIS[O-(2-METHOXYETHOXY)METHYLOXIME]

The procedure used is as in Example 27, tylosin (E+Z)-9,20-dioxime being replaced by demycarosyldemycinosyltylosin (E+Z)-9,20-dioxime, obtained in Example 29.
Spectral characteristics:
Mass spectrometry:
[M—H]+:M/Z:948

EXAMPLE 43: CARBOMYCIN B (E+Z)-9-OXIME OR 9[(E+Z)-HYDROXYIMINO]-9-DEOXYCARBOMYCIN B

STAGE A: Carbomycin B or dihydroleucomycin A$_3$ 10.0 g (12.1 mmol) of leucomycin A$_3$, also known as josamycin, are dissolved in 30 ml of DMSO and 15 ml of triethylamine. To the solution thereby obtained, 5.6 g of sulfur trioxide/pyridine complex (36.3 mmol), dissolved in 40 ml of DMSO, are added at room temperature and under a nitrogen atmosphere. The reaction medium is stirred at room temperature for 3 hours. Approximately 200 g of ice are added and the mixture is filtered: the product thereby obtained is taken up with methylene chloride and the organic phase is washed three times with water; the organic phase is dried over sodium sulfate, filtered and evaporated to dryness. The residue thereby obtained is purified by flash chromatography on a silica column; eluant: CH$_2$Cl$_2$/MeOH/NH$_4$OH (300:5:0.25). 3.6 g of carbomycin B are obtained.
Yield: 36.4%

STAGE B: Carbomycin B 18-(dimethyl acetal) or 18-dimethoxy-18-deoxycarbomycin B 2.8 g (3.4 mmol) of carbomycin B, obtained above, are dissolved in 30 ml of methanol. 0.65 g (3.4 mmol) of para-toluenesulfonic acid monohydrate is added. The solution obtained is stirred for 50 minutes; 1.7 ml of triethylamine are then added and stirring is maintained for 30 minutes. The methanol is evaporated off, the residue is taken up with 80 ml of dichloromethane and the mixture is washed with water. The organic phase is dried over sodium sulfate, filtered and evaporated to dryness. The residue obtained is purified by flash chromatography on a silica column using a 25:1:0.05 CH$_2$Cl$_2$/CH$_3$OH/NH$_4$OH mixture as eluant. 2.0 g of carbomycin B 18-(dimethyl acetal), or 18-dimethoxy-18-deoxycarbomycin B, are obtained.
Yield: 68%

STAGE C: carbomycin B 18-(dimethyl acetal) (E+Z) -9-oxime or 9,18-dideoxyl-9-[(E+Z)-hydroxyiminol]-18-dimethoxycarbomycin B 1.5 g. (17 mmol) of carbomycin B 18-(dimethyl acetal) are dissolved in 10 ml of pyridine. 354 mg (51 mmol) of hydroxylamine hydrochloride are added and the solution obtained is stirred for 24 hours at room temperature. Ice is added and the mixture is extracted with dichloromethane. The extract is dried over sodium sulfate, filtered and evaporated to dryness. The residue obtained is purified by flash chromatography using a 300:5:0.25 CH$_2$Cl$_2$/MeOH/NH$_4$OH mixture as eluant. 1.2 g of carbomycin B dimethyl acetal (E+Z)-9-oxime are obtained.
Yield: 71%

STAGE D: Carbomycin B (E+Z)-9-oxime or 9-hydroxyimino-9-deoxycarbomycin B 1.2 g of carbomycin B 18-(dimethyl acetal) (E+Z) -9-oxime (1.35 mmol) are dissolved in 100 ml of an acetonitrile/water (1:1 v/v) mixture. Five equivalents (0.47 ml) of difluoroacetic acid are added and the mixture is stirred for 3 days at room temperature. 3 ml of triethylamine are added and stirring is maintained for 1 hour. The acetonitrile is evaporated off on a waterbath under vacuum and the residue is extracted three times with 80 ml of dichloromethane. The extracts are dried over sodium sulfate and filtered and the solvent is evaporated off to dryness. The residue obtained is purified by flash chromatography on a silica column; eluant-:methylene chloride/methanol/ammonia solution (300:5:0.25). 600 mg of oxime are obtained.
Yield: 53%
Empirical formula: C$_{42}$H$_{68}$N$_2$0$_{15}$
Molecular weight: 840.98
Spectral characteristics:
$^1$H NMR solvent CDCl$_3$ 200 MHz
δ=3.40, singlet, 3H, CH$_3$ R$_4$ substituent
δ=3.71, singlet, 1H, H$^5$
δ=9.20, singlet, 1H, aldehyde, C$^{18}$
$^{13}$C NMR solvent CDCl$_3$
δ=84.9 ppm, C$^5$
δ=201.4 ppm, C$^{18}$
Mass spectrometry:
[M—H]+:M/Z:841

EXAMPLE 44: CARBOMYCIN B (E+Z)-9-(O-BENZYLOXIME OR 9-[(E+Z)-BENZYLOXYIMINO]-9-DEOXYCARBOMYCIN B

STAGE A: Carbomycin B 18-(dimethyl acetal) (E+Z) -9-(O-benzyloxime)

1.5 g of carbomycin B 18-(dimethyl acetal) (17 mmol) obtained in Example 43, Stage B, are dissolved in 10 ml of pyridine. 820 mg (51 mmol) of benzyloxyamine hydrochloride are added. The mixture is stirred for 3 days at room temperature. Ice is added and the mixture is extracted with CH$_2$Cl$_2$. The extract is dried over Na$_2$SO$_4$, filtered and evaporated to dryness. The product obtained is purified by flash chromatography on a silica column using a 50:1:0.2 CH$_2$Cl$_2$/methanol/ammonia solution mixture as eluant. 1.2 g of expected product are obtained.

Yield: 70%

STAGE B: Carbomycin B (E+Z)-9-(O-benzyloxime)

1.2 g (1.23 mmol) of carbomycin B 18-(dimethyl acetal) (E+Z)-9-(O-benzyloxime) are dissolved in 100 ml of an acetonitrile/water (1:1 v/v) mixture. 0.5 ml of difluoroacetic acid is added. The mixture is stirred for 4 days at room temperature, 15 equivalents of triethylamine (3 ml) are then added and the mixture is stirred for 1 hour. The acetonitrile is evaporated off on a water-bath under vacuum and the residue is extracted with methylene chloride. The extract is dried over sodium sulfate, filtered and evaporated to dryness. The residue obtained is purified by flash chromatography using a methylene chloride/methanol/ammonia solution (200:2.5:0.15) mixture as eluant. 500 mg of the expected product are obtained.

Yield: 45%
Empirical formula: C$_{49}$H$_{74}$N$_2$O$_{15}$
Molecular weight: 931.1
Spectral characteristics:
$^1$H NMR solvent CDCl$_3$ 200 MHz
$\delta$=3.55, singlet, 3H, COCH$_3$ (R$_4$)
$\delta$=5.10, singlet, 2H, CH$_2$—C$_6$H$_5$
$\delta$=7.20, singlet, 5H, benzene ring
$\delta$=9.30, singlet, 1H, aldehyde.
$^{13}$C NMR solvent CDCl$_3$
$\delta$=155.8 ppm C$^9$
$\delta$=169.8 ppm C$^1$
$\delta$=201.1 ppm C$^{18}$

EXAMPLE 45:
9-BENZYLOXYIMINO-9-DEOXYDE(4"-ISO-VALERYLMYCAROSYL)CARBOMYCIN B

By the procedure used in Example 44, after the elution of 9-[(E+Z)-benzyloxyimino]-9-deoxycarbomycin B, 9-[(E+Z)-benzyloxyimino]-9-deoxyde(4"-isovalerylmycarosyl) -carbomycin B is obtained in Stage B.

Yield: 20%
Empirical formula: C$_{37}$H$_{54}$N$_2$O$_{11}$
Molecular weight: 702.8
Spectral characteristics:
$^1$H NMR solvent CDCl$_3$ 200 MHz
$\delta$=3.53 ppm, singlet, 3H, CO—CH$_3$(R$_4$)
$\delta$=7.30 ppm, singlet, 5H, benzene ring
$\delta$=9.40 ppm, singlet, H, aldehyde.
$^{13}$C NMR solvent CDCl$_3$
$\delta$=156 ppm, C$^9$
$\delta$=170 ppm, C$^1$
$\delta$=201.3 ppm, C$^{18}$
Mass spectrometry (F.A.B.):
[M—H]$^+$:M/Z:703

EXAMPLE 46:
9-[(E+Z)-METHYLOXYIMINO]-9-DEOXYCARBOMYCIN B

By the procedure used in Example 44, and benzyloxyamine hydrochloride being replaced by methyloxyamine hydrochloride, the expected product is obtained.

EXAMPLE 47:
9-[(E+Z)-METHYLOXYIMINO]-9-DEOXYDE-(4"-ISOVALERYLMYCAROSYL)CARBOMYCIN B

By the procedure used in Example 45, and benzyloxyamine hydrochloride being replaced by methyloxyamine hydrochloride, the expected product is obtained.
Spectral characteristics:
Mass spectrometry:
[M—H]$^+$:M/Z:627

EXAMPLES 48 AND 49:

In the same manner as in Example 46, methyloxyamine hydrochloride being replaced by:
O-allylhydroxylamine hydrochloride (EXAMPLE 48),
O-ehtylhydroxylamine hydrochloride (EXAMPLE 49), the following are obtained:

EXAMPLE 48:
9-[(E+Z)-ALLYLOXYIMINO]-9-DEOXYCARBOMYCIN B

EXAMPLE 49:
9-[(E+Z)-ETHYLOXYIMINO]-9-DEOXYCARBOMYCIN B

EXAMPLE 50 AND 51:

In the same manner as in Example 47, methyloxyamine hydrochloride being replaced by:
O-allylhydroxylamine hydrochloride (EXAMPLE 50),
O-ethylhydroxylamine hydrochloride (EXAMPLE 51), the following are obtained:

EXAMPLE 50:
9-[(E+Z)-ALLYLOXYIMINO]-9-DEOXYDE(4"-ISOVALERYLMYCAROSYL)CARBOMYCIN B

EXAMPLE 51:
9-[(E+Z)-ETHYLOXYIMINO]-9-DEOXYDE(4"-ISOVALERYLMYCAROSYL)CARBOMYCIN B

EXAMPLE 52: CARBOMYCIN B (E+Z)-9-{O-[(2-METHOXYETHOXY) METHYL]OXIME} OR 9-{(E+Z)-[(2-METHOXYETHOXY)METHYL]-OXYIMINO}-9-DEOXYCARBOMYCIN B 0.46 g (0.52 mmol) of carbomycin B 18-(dimethyl acetal) (E+Z)-9-oxime, obtained in Example 43, Stage C, is dissolved in 10 ml of tetrahydrofuran. The procedure is then as in Example 7, Stages B and C, to obtain the expected product.

EXAMPLE 53: CARBOMYCIN B (E+Z)-9-{O-[2-(VINYLOXY) ETHYL]OXIME}

By the procedure used in the preceding example, but (2-methoxyethoxy)methyl chloride being replaced by 2-chloro-1-(vinyloxy)ethane, the expected product is obtained.

EXAMPLE 54: CARBOMYCIN B (E+Z)-9-[O-(2-DIMETHYLAMINOETHYL) OXIME]

2.0 g (2.25 mmol) of carbomycin B 18-(dimethyl acetal) (E+Z)-9-oxime, obtained in Example 43, are dissolved in 45 cm$^3$ of tetrahydrofuran, and the procedure is then the same as in Example 15.

EXAMPLE 55: CARBOMYCIN B (E+Z)-9-[O-(2-DIMETHYLAMINO-1-METHYLETHYL)OXIME]

By the procedure used in Example 54, but 1-chloro-2-dimethylaminoethane hydrochloride being replaced by 2-chloro-1-dimethylaminopropane hydrochloride, carbomycin B (E+Z)-9-[O-(2-dimethylamino-1-methylethyl)oxime] is obtained.

EXAMPLE 56: CARBOMYCIN B (E+Z)-9-{O-[2-(4-MORPHOLINYL)ETHYL]OXIME}

2.0 g (2.25 mmol) of carbomycin B dimethyl acetal (E+Z)-9-oxime, obtained in Example 43, is dissolved in 45 cm$^3$ of tetrahydrofuran, and the procedure is then the same as in Example 19.

EXAMPLE 57: CARBOMYCIN B (E+Z)-9-{O-[2-(1-PYRROLIDINYL)ETHYL]OXIME}

By the replacement of 4-(2-chloroethyl)morpholine hydrochloride in the preceding example by 1-(2-chloroethyl)-pyrrolidine hydrochloride, the expected product is obtained.

EXAMPLE 58: CARBOMYCIN B (E+Z)-9-{O-[2-(1-PIPERIDYL) ETHYL]OXIME}

By the replacement of 4-(2-chloroethyl)morpholine hydrochloride in Example 56 by 1-(2-chloroethyl)-piperidine hydrochloride, the expected product is obtained.

EXAMPLE 59: CARBOMYCIN B (E+Z)-9,18-DIOXIME 2.8 g (3.4 mmol) of carbomycin B, obtained in Example 43, Stage A, are dissolved in 20 ml of pyridine. 2.36 g (34 mmol) of hydroxylamine hydrochloride are added and the solution obtained is stirred for 48 hours at room temperature. The reaction medium is diluted with water and extracted with dichloromethane. The extract is dried over sodium sulfate, filtered and evaporated to dryness. The residue obtained is purified by flash chromatography on a silica column using a $CH_2Cl_2$/MeOH/$NH_4OH$ mixture as eluant.

Spectral characteristics:
Mass spectrometry:
[M—H]$^+$:M/Z:856

EXAMPLE 60: 9,18-BIS[(E+Z)-METHOXYIMINO]-9,18-DIDEOXYCARBOMYCIN B

By the procedure used in Example 59, but hydroxylamine hydrochloride being replaced by methoxyamine hydrochloride, the expected product is obtained.

EXAMPLE 61: CARBOMYCIN B 9,18-BIS[(E+Z)-O-(2-METHOXYETHOXY)METHYLOXIME]

2 g (2.34 mmol) of carbomycin B (E+Z)-9,18-dioxime are dissolved in 40 cm$^3$ of tetrahydrofuran, and the procedure is then as in Example 27. The expected product is obtained.

EXAMPLE 62: 9-[(E+Z)-(2-METHOXYETHOXY)METHOXYIMINO]-18-METHOXYIMINO-9,18-DIDEOXYCARBOMYCIN B 2 g (2.15 mmol) of 9-[(E+Z)-(2-methoxyethoxy)methoxyimino]-9-deoxycarbomycin B, obtained in Example 52, are dissolved in 5 ml of pyridine. 650 mg (65 mmol) of methoxyamine hydrochloride are added. The mixture is stirred for 3 days at room temperature. The reaction medium is diluted using ice-cold water and extracted with methylene chloride. The extract is dried over sodium sulfate, filtered and evaporated to dryness. The residue is purified by flash chromatography on a silica column using a $CH_2Cl_2$/methanol/ammonia solution mixture as eluant. The expected product is obtained.

EXAMPLE 63: 9-[(E+Z)-(PARA-NITROBENZYLOXYIMINO)]-9-EOXYCARBOMYCIN B

By the replacement of benzyloxyamine hydrochloride in Example 44 by para-nitrobenzyloxyamine hydrochloride, the expected product is obtained.

EXAMPLE 64: 9-[(E+Z)-(PARA-NITROBENZYLOXYIMINO)]-TYLOSIN

By the replacement of benzyloxyamine hydrochloride in Example 6 by para-nitrobenzyloxyamine hydrochloride, the expected product is obtained.

EXAMPLE 65: STUDY OF THE ACTIVITY OF THE COMPOUNDS OF FORMULA (I) WITH RESPECT TO VARIOUS BACTERIAL STRAINS

The determination of the minimal inhibitory concentrations (MIC) is performed:
for staphylococci and enterococci (D streptococci), in agar medium or in MUELLER HINTON fluid;
for Haemophilus strains, non-D streptococci and Neisseria gonorrhoeae, the determination of the MIC values is performed according to the method of dilution in cooked blood-containing agar medium enriched with Polyvitex* medium. Culturing is carried out in an atmosphere enriched with $CO_2$.

The reading of the MIC values is performed after 18 hours' incubation at 37° C.

The products are tested in the concentration range from 0.125 to 256 mg/l (successive two-fold dilutions).

The minimal inhibitory concentrations are of the order of:
1 mg.ml$^{-1}$ for Staphylococcus aureus, B, C, D and G streptococci and pneumococci;
0.5 mg/ml$^{-1}$ for A streptococci;
0.1 mg/ml$^{-1}$ for Neisseria gonorrhoeae.

These studies collectively show the advantageous antibiotic activity of the compound of the invention, both in respect of the intensity of its activity and also in respect of the breadth of its spectrum of action.

EXAMPLE 66: PHARMACEUTICAL COMPOSITIONS: TABLET

Tablets containing a 100 mg dose of 9-[(E+Z)-(2-methoxyethoxy)methoxyimino]-9-tylosin

| | |
|---|---|
| 9-[(E + Z)-(2-Methoxyethoxy)methoxyimino]-9-deoxycarbomycin B | 100 g |

| -continued | |
|---|---|
| Wheat Starch | 70 g |
| Cornstarch | 60 g |
| Lactose | 60 g |
| Magnesium stearate | 9 g |
| Silica | 4 g |
| Hydroxypropylcellulose | 7 g |

Preparation formula for 1000 tablets.

We claim:

1. A compound selected from those of the formula:

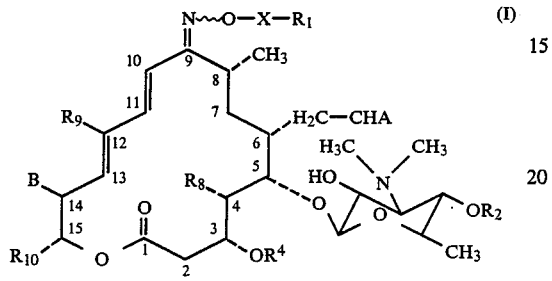

in which
- A denotes: either an oxygen atom, or a group of formula N~O—Y—R$_5$, the sign ~ present in the substituent of carbon$^9$ as well as in the definition of A meaning that one or other, independently, of the oxime or oxime ether groups can each be in the syn or anti form or in the form of a syn and anti mixture,
- X and Y, which may be identical or different, denote either a linear or branched alkyl radical containing at most ten carbon atoms, or a linear or branched alkenyl radical containing at most ten carbon atoms,
- R$_1$ and R$_5$, which may be identical or different, denote:
  either a hydrogen atom,
  or a linear or branched alkyloxy radical containing at most ten carbon atoms, or a linear or branched alkenyloxy radical containing at most ten carbon atoms, or a phenyl radical which radicals maybe optionally substituted with one or more radicals selected from, lower alkyl, lower alkyloxy, fluoro, chloro, bromo, iodo, nitro,
  or a radical

in which R$_6$ and R$_7$, which may be identical or different, denote a hydrogen atom or a lower alkyl radical, or form, with the nitrogen, a 5- or 6-membered heterocyclic system which may contain one additional hetero atom and which may be substituted with a halogen atom or a lower alkyl radical, a chlorine, bromine, iodine or fluorine atom,
or X—R$_1$ and Y—R$_5$, independently of one another, each denote a hydrogen atom,
R$_2$ denotes a hydrogen atom, or a radical of formula:

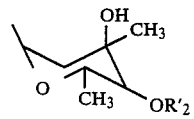

in which R'$_2$ denotes a hydrogen atom, an alkyl radical or a linear or branched lower acyl radical,
B denotes
  a hydrogen atom,
  or a radical of formula: —CH$_2$—O—B', where B' denotes:
    either a hydrogen atom,
    or a radical of formula:

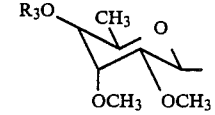

in which R$_3$ denotes a hydrogen atom or a linear or branched lower alkyl radical,
R$_4$ denotes
  a hydrogen atom,
  or a linear or branched lower alkyl radical,
  or a linear or branched lower acyl radical,
R$_8$ denotes
  a lower alkyl radical when B denotes a group—CH$_2$—O—B',
  or a lower alkyloxy radical when B denotes a hydrogen atom,
R$_9$ denotes
  a hydrogen atom when B denotes a hydrogen atom,
  or a lower alkyl radical when B denotes a radical —CH$_2$—O—B',
R$_{10}$ denotes a lower alkyl radical, the term lower, referring to the lower alkyl and lower alkyloxy radicals, denoting that the groups in question contain between 1 and 6 carbon atoms, and their addition salts with an acid.

2. The compound as claimed in claim 1, in which A denotes an oxygen atom, their (Z) or (e) isomers, isolated or in the form of a mixture, as well as their addition salts with a pharmaceutically acceptable acid.

3. The compound as claimed in claim 1, in which A denotes a group of formula N O—Y—R$_5$, their (Z) or (e) isomers, isolated or in the form of a mixture, as well as their addition salts with a pharmaceutically acceptable acid.

4. The compound as claimed in claim 3, in which Y—R$_5$ has the same meaning as X—R$_1$, as well as their (Z) or (E) isomers, isolated or in the form of a mixture, as well as their addition salts with a pharmaceutically acceptable acid.

5. The compound as claimed in claim 1, in which:
A denotes an oxygen atom,
X is a linear or branched lower alkyl radical,
R$_1$ is
  a hydrogen atom,
  an aryl group which may be substituted with a nitro group,
  an alkenyloxy radical,
  an alkyloxy radical which may be substituted with a lower alkyloxy radical,
  a dialkylamino radical, a nitrogen-containing heterocycle optionally containing at most two hetero atoms, which may be substituted with halo or lower-alkyl, or alternatively X—R₁ denotes a hydrogen atom, their (Z) or (E) isomers, isolated or in the form of a mixture, as well as their addition salts with a pharmaceutically acceptable acid.

6. The compound as claimed in claim 3, in which:
Y is a lower alkyl radical,
R₅ is a hydrogen atom or an alkyl radical or an alkyloxy radical optionally substituted with a lower alkyloxy radical, or Y—R₅ denotes a hydrogen atom, their (Z) and (E) isomers, isolated or in the form of a mixture, as well as their addition salts with a pharmaceutically acceptable acid.

7. The compound as claimed in claim 1, in which B' and R₂ simultaneously denote a hydrogen atom, their (Z) or (E) isomers, isolated or in the form of a mixture, as well as their addition salts with a pharmaceutically acceptable acid.

8. The compound as claimed in claim 1, in which B and R₉ simultaneously denote a hydrogen atom, R₈ a methoxy group and R₁₀ a methyl group, their (Z) and (E) isomers, isolated or in the form of a mixture, as well as their addition salts with a pharmaceutically acceptable acid.

9. The compound as claimed in claim 1, in which B denotes a group of formula:

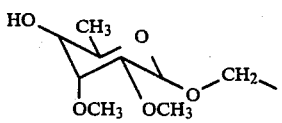

and R₈ and R₉ simultaneously denote a methyl group and R₁₀ an ethyl group, their (Z) and (E) isomers, isolated or in the form of a mixture, as well as their addition salts with a pharmaceutically acceptable acid.

10. The compound as claimed in claim 1, which is tylosin 9-oxime, its (Z) and (E) isomers, isolated or in the form of a mixture, as well as its addition salts with a pharmaceutically acceptable acid.

11. The compound as claimed in claim 1, which is tylosin 9-(O-methyloxime), its (Z) and (E) isomers, isolated or in the form of a mixture, as well as its addition salts with a pharmaceutically acceptable acid.

12. The compound as claimed in claim 1, which is tylosin 9-(O-benzyloxime), its (Z) and (E) isomers, isolated or in the form of a mixture, as well as its addition salts with a pharmaceutically acceptable acid.

13. The compound as claimed in claim 1, which is tylosin 9-{O-[(2-methoxyethoxy)methyl]oxime}, its (Z) and (E) isomers, isolated or in the form of a mixture, as well as its addition salts with a pharmaceutically acceptable acid.

14. The compound as claimed in claim 1, which is tylosin 9,20-dioxime, its (Z) and (E) isomers, isolated or in the form of a mixture, as well as its addition salts with a pharmaceutically acceptable acid.

15. The compound as claimed in claim 1, which is demycarosylthylosin 9-oxime, its (Z) and (E) isomers, isolated or in the form of a mixture, as well as its addition salts with a pharmaceutically acceptable acid.

16. The compound as claimed in claim 1, which is demycarosyltylosin 9-(O-methyloxime), its (Z) and (E) isomers, isolated or in the form of a mixture, as well as its addition salts with a pharmaceutically acceptable acid.

17. The compound as claimed in claim 1, which is demycarosyltylosin 9-(O-benzyloxime), its (Z) and (E) isomers, isolated or in the form of a mixture, as well as its addition salts with a pharmaceutically acceptable acid.

18. The compound as claimed in claim 1, which is demycarosyltylosin 9-{O-[(2-methoxyethoxy) methyl]oxime}, its (Z) and (E) isomers, isolated or in the form of a mixture, as well as its addition salts with a pharmaceutically acceptable acid.

19. The compound as claimed in claim 1, which is demycarosyltylosin 9,20-dioxime, its (Z) and (E) isomers, isolated or in the form of a mixture, as well as its addition salts with a pharmaceutically acceptable acid.

20. The compound as claimed in claim 1, which is 9-[(E+Z)-hydroxyimino]-9-deoxycarbomycin B, its (Z) and (E) isomers, isolated or in the form of a mixture, as well as its addition salts with a pharmaceutically acceptable acid.

21. The compound as claimed in claim 1, which is 9-[(E+Z)-methoxyimino]-9-deoxycarbomycin B, its (Z) and (E) isomers, isolated or in the form of a mixture, as well as its addition salts with a pharmaceutically acceptable acid.

22. The compound as claimed in claim 1, which is 9-[(E+Z)-benzyloxyimino]-9-deoxycarbomycin B, its (Z) and (E) isomers, isolated or in the form of a mixture, as well as its addition salts with a pharmaceutically acceptable acid.

23. The compound as claimed in claim 1, which is 9-[(E+Z)-(para-nitrobenzyloxyimino)]-9-deoxycarbomycin B, its (Z) and (E) isomers, isolated or in the form of a mixture, as well as its addition salts with a pharmaceutically acceptable acid.

24. The compound as claimed in claim 1, which is 9-{O-[(2-methoxyethoxy)methyl]oxyimino}-9-deoxycarbomycin B, its (Z) and (E) isomers, isolated or in the form of a mixture, as well as its addition salts with a pharmaceutically acceptable acid.

25. A pharmaceutical composition containing as active agent an antibacterially-effective amount of at least one compound as claimed in claim 1, in combination with one or more pharmaceutically acceptable, non-toxic, inert vehicles or excipients.

26. The pharmaceutical composition as claimed in claim 25, wherein the antibacterially-effective amount is 0.01 to 4 grams.

27. A method for treating a living animal afflicted with a bacterial infection comprising the step of administering to the said living animal an amount of a compound of claim 1 which is suitable for alleviation of said condition.

28. The compound of claim 1 wherein R⁸ denotes methyl.

29. The compound of claim 1 wherein R⁸ denotes methoxy.

30. The compound of claim 1 wherein R⁹ denotes methyl.

* * * * *

UNITED STATES PATENT AND TRADEMARK OFFICE
CERTIFICATE OF CORRECTION

PATENT NO. : 4,918,058

DATED : April 17, 1990

INVENTOR(S) : Gabor Lukacs, Catherine Duchatelle-Ruggeri

Page 1 of 2

It is certified that error appears in the above-identified patent and that said Letters Patent is hereby corrected as shown below:

Column 1, line 38; "carbon as" should read -- carbon$^9$ as --.
Column 2, line 10; "aralkylthd" should read -- aralkylthio --.
Column 3, line 54; "N    -O" should read -- N$\frown$-O --.
Column 3, line 55; "sign    has" should read -- sign$\frown$has --.
Column 5, line 14; "R'$_2$," should read -- R$_2$, --.
Column 5/6, 1st formula, far right, "OR$_1$" should read -- OR$_2$ --.
Column 7, line 58; "in" should read -- is --.
Column 11, line 2; "gonorhoeae" should read -- gonorrhoea --.
Column 12, line 5; "MeOH+100:4." should read -- MeOH = 100 : 4. --.
Column 13, line 28; "DEMYCAROSYTYLOSIN" should read
    -- DEMYCAROSYLTYLOSIN --.
Column 15, line 26; "Tylosing" should read -- Tylosin --.
Column 16, line 17; ")CH$_3$" should read -- OCH$_3$) --.
Column 20, line 65; "80%" should read -- 86% --.
Column 24, line 9; "-dideoxyl-" should read -- dideoxy- --.
Column 26, line 18; "O-ehtylhydroxylamine" should read
    -- O-ethylhydroxylamine --.
Column 28, line 21; "EOXYCARBOMYCIN B" should read
    -- DEOXYCARBOMYCIN B --.
Column 28, line 41; "gonorrhoeae" should read -- gonorrhoea --.

UNITED STATES PATENT AND TRADEMARK OFFICE
CERTIFICATE OF CORRECTION

PATENT NO. : 4,918,058
DATED : April 17, 1990
INVENTOR(S) : Gabor Lukacs, Catherine Duchatelle-Ruggeri It is certified that error appears in the above-identified patent and that said Letters Patent is hereby corrected as shown below:

Column 28, line 55; "gonorrhoeae" should read -- gonorrhoea --.
Column 29, line 46; "maybe" should read -- may be --.

Column 30, line 45; "(e)" should read -- (E) --.
Column 30, line 49; "N   O" should read -- N/N/O --.

Signed and Sealed this

Thirteenth Day of August, 1991

Attest:

HARRY F. MANBECK, JR.

Attesting Officer          Commissioner of Patents and Trademarks